United States Patent
Liang et al.

(10) Patent No.: US 7,374,551 B2
(45) Date of Patent: May 20, 2008

(54) MINIMALLY INVASIVE FAT CAVITATION METHOD

(75) Inventors: Marc D. Liang, Pittsburgh, PA (US); Krishna Narayanan, Pittsburgh, PA (US)

(73) Assignee: Pittsburgh Plastic Surgery Research Associates, Pittsburgh, PA (US)

( * ) Notice: Subject to any disclaimer, the term of this patent is extended or adjusted under 35 U.S.C. 154(b) by 509 days.

(21) Appl. No.: 10/370,214

(22) Filed: Feb. 19, 2003

(65) Prior Publication Data

US 2004/0162546 A1  Aug. 19, 2004

(51) Int. Cl.
*A61B 17/20* (2006.01)

(52) U.S. Cl. ............... 604/22; 606/128; 128/24
(58) Field of Classification Search ............ 128/24; 604/22; 606/128
See application file for complete search history.

(56) References Cited

U.S. PATENT DOCUMENTS

| | | | |
|---|---|---|---|
| 4,474,180 A | 10/1984 | Angulo | |
| 4,750,488 A | 6/1988 | Wuchinich et al. | |
| 4,750,902 A | 6/1988 | Wuchinich et al. | |
| 4,867,141 A | 9/1989 | Nakada et al. | |
| 4,886,491 A * | 12/1989 | Parisi et al. | 604/22 |
| 4,920,954 A * | 5/1990 | Alliger et al. | 606/128 |
| 5,052,999 A * | 10/1991 | Klein | 604/19 |
| 5,123,903 A | 6/1992 | Quaid et al. | |
| 5,419,761 A * | 5/1995 | Narayanan et al. | 604/22 |
| 5,527,273 A | 6/1996 | Manna et al. | |
| 5,725,494 A | 3/1998 | Brisken | |
| 5,728,062 A * | 3/1998 | Brisken | 604/22 |
| 5,957,943 A | 9/1999 | Vaitekunas | |
| 5,989,274 A | 11/1999 | Davison et al. | |
| 6,149,620 A | 11/2000 | Baker et al. | |

(Continued)

OTHER PUBLICATIONS

Addicted to Lipo, *Vogue*, pp. 368-371, Oct. 2002.

(Continued)

*Primary Examiner*—Brian L. Casler
*Assistant Examiner*—John F. Ramirez
(74) *Attorney, Agent, or Firm*—Matthew W. Gordon, Esq.; Alan G. Towner, Esq.; Pietragallo Gordon Alfano Bosick & Raspanti, LLP (57) ABSTRACT

A method of fat cavitation including infiltrating adipose tissue with a liquid, creating a puncture in a patient's skin, providing a wire, the wire being generally uniform in diameter and having a first end and a second end and introducing the second end of the wire through the puncture in the patient's skin. The method further includes placing at least a portion of the second end of the wire in contact the adipose tissue, generating an ultrasonic wave, transmitting the ultrasonic wave to the second end of the wire, creating cavitation bubbles in at least a portion of the targeted adipose tissue and liquefying at least a portion of the targeted adipose tissue. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims.

23 Claims, 4 Drawing Sheets

U.S. PATENT DOCUMENTS

| | | |
|---|---|---|
| 6,221,038 B1 | 4/2001 | Brisken |
| 6,283,974 B1 | 9/2001 | Alexander |
| 6,296,620 B1 | 10/2001 | Gesswein et al. |
| 6,387,109 B1 | 5/2002 | Davison et al. |
| 6,413,216 B1 | 7/2002 | Cain et al. |
| 6,432,068 B1 | 8/2002 | Corl et al. |
| 6,626,854 B2 * | 9/2003 | Friedman et al. .............. 601/2 |

OTHER PUBLICATIONS

Michele L. Zocchi, M.D., Ph.D., Ultrasonic Assisted Lipoplasty—Technical Refinements and Clinical Evaluations, *Clinics in Plastic Surgery*, vol. 23 No. 4, pp. 575-598, Oct. 1996, From Aesthetic Plastic and Reconstructive Surgery, Torino, Italy.

Michele L. Zocchi, M.D., Ph.D., Ultrasonic-Assisted Lipectomy, *Advances in Plastic and Reconstructive Surgery*, vol. 11, pp. 197-221, 1995, Mosby—Year Book, Inc.

Douglas L. Miller, A Review Of The Ultrasonic Bioeffects Of Microsonation, Gas-Body Activation, And Related Cavitation-Like Phenomena, *Ultrasound in Med. & Biol.*, vol. 13, No. 8, pp. 443-470, 1987, Pergamon Journals Ltd.

David J. Galton, M.Sc., M.D., M.R.C.P., Lipolysis and its Control, *The Human Adipose Cell: A Model for Errors in Metabolic Regulation*, pp. 105-114, 1971, New York Appleton-Century-Crofts, Division of Meredith Corporation, Printed offset in Great Britain by The Camelot Press Ltd., London and Southampton.

* cited by examiner

Stepped

(Prior Art)
FIG. 6(a)

Conical (Prior Art)
FIG. 6(b)

e-x Taper (Prior Art)
FIG. 6(c)

MINIMALLY INVASIVE FAT CAVITATION METHOD

BACKGROUND OF THE TECHNOLOGY

1. Field of the Invention

The present disclosure relates to a minimally invasive method of fat cavitation.

2. Description of the Background of the Technology

Cosmetic surgery, which is mainly consumer driven, represents one of the fastest growing areas in medicine. As people age, they, along with their children, spend millions of dollars each year on cosmetic and aesthetic improvements. Liposuction is one of the most frequently requested of these cosmetic procedures. The American Society of Plastic Surgeons (ASPS) reports that there were over 400 thousand liposuction procedures performed in 2001, making it one of the five most frequently performed cosmetic procedures in the United States. According to the ASPS 2000 national statistics, the total number of liposuction procedures performed in the United States was 354,015. There is a strong rate of growth in the number of procedures performed every year. Recently, there is an increase in the number of micro-liposuction procedures.

More than 50% of the population of the United States is overweight or obese—this fact is well established. For this segment of the population, plastic and cosmetic surgeries play a complementary role to weight loss training and personal training in improving their quality of life.

The target of liposuction, adipose tissue, is found in the innermost layer of the skin, the subcutaneous layer. The outermost layer of the skin is known as the epidermis, while the intermediate layer is known as the dermis. Fat lysis is a procedure which results in the permanent reduction of adipose tissue. The most commonly accepted liposuction technique utilizes a cannula with a blunt closed tip rather than an open tip or a pointed or sharpened tip. This cannula is a metal tube, about the size of a pencil, which is attached to a suction pump. The cannula, with its rounded tip, is sometimes passed through the fat first, without suction, to develop the proper passageways. Then suction is applied and the surgeon continues passing the cannula through the fat tunnels with repeated radial thrusts and on several levels of the tissue. Adipose tissue is aspirated through a hole in the side of the cannula near its distal end. The cannula must be moved back and forth several times through each tunnel. Problems associated with this technique are similar to those experienced with the older methods of liposuction. Even with a blunt edge at the distal end of the cannula, fat globules are torn off by both scraping and suction power at the side hole. The bleeding is also similar in amount to that resulting from the use of the older, sharp-edged instruments which cut fat tissue and blood vessels without suction.

An alternative technique involves the addition of high frequency ultrasound to traditional liposuction. This procedure typically employs titanium cannulas through which ultrasonic waves are passed. The ultrasonic waves result in disruption of the adipose tissue, making suction of the emulsified adipose tissue through the cannula a somewhat easier process. Another variant includes the use of external ultrasound on the skin overlying the adipose tissue followed by traditional liposuction. With this external application of ultrasound, the adipose tissue is probably dispersed in the tumescent medium prior to being removed through suction.

The safety and efficacy of liposuction have improved over the last twenty years since the treatment began in the United States. Nevertheless, it still has many disadvantages. Complications from liposuction arise from damaged blood vessels. As a result, organized semi-solid blood clots known as "hematoma" form causing damage to overlying skin, as well as contour irregularities. Other complications, such as seroma formation (the collection of body fluids) can produce infection and wrinkles. Nerve conduction may also be affected. Further, too much fat is sometimes removed from the wrong site, resulting in a misshaping of the surrounding tissue. Lastly, liposuction procedures are time consuming and tedious for both the surgeon and the patient.

As mentioned above, conventional liposuction treatment has been enhanced by the use of ultrasound. Following a surgical incision, a probe is inserted into a target area of adipose tissue in a patient. Ultrasonic waves, emanating from a transducer, are transmitted to the adipose tissue via the probe, forming cavitation bubbles and resulting in the liquefaction of that tissue. A transducer which converts electrical energy into mechanical vibrations may be located external to, or be incorporated into, the probe. The liquefied adipose tissue is then aspirated through a suction tube. While this procedure represents a clear improvement over standard liposuction, it still requires a surgical incision, which results in scarring of the skin surface, and significant recovery time for the patient of about 3-6 weeks.

SUMMARY

A process for ablating adipose tissue, without the need for the use of general anesthesia or an incision requiring sutures, which allows the patient to continue with daily activities with virtually no recovery time would be highly advantageous.

U.S. Pat. No. 4,920,954, entitled, "Ultrasonic Device for Applying Cavitation Forces," and issued to Alliger et al. and U.S. Pat. No. 4,474,180, entitled, "Apparatus for Disintegrating Kidney Stones," and issued to Angulo are incorporated herein by reference in their entirety. The methods described herein may be carried out using the devices of the type set forth in U.S. Pat. No. 4,920,954 and U.S. Pat. No. 4,474,180 or any other device which includes a catheter with a wire disposed therein, the wire being connected to, or in communication with, a horn which in turn is connected to, or in communication with, a generator. Such devices are common and well known to those of ordinary skill in the art.

As used herein, the term "cavitation" means the formation of bubbles or cavities in tissue. When adipose tissue is cavitated, it liquefies, ire., it is transformed into a liquid state.

High frequency energy is that which is over 16 kHz—too high to be perceived by the human ear.

As used herein, "microbubble" means an extremely small bubble. The maximum size of a microbubble is dictated by the inner diameter of the syringe needle or inner diameter of the catheter through which it is introduced to the targeted adipose tissue—a microbubble must be small enough to pass through either of these inner diameters and, as such is typically so small that it would not appear as a bubble to the naked eye.

As used herein, "generally uniform in diameter" refers to a physical characteristic of a wire whereby it does not have an enlarged head on its second (or distal) end.

One embodiment of the present disclosure contemplates a method of fat cavitation, including infiltrating adipose tissue with a liquid, creating a puncture in a patient's skin and providing a wire, the wire being generally uniform in diameter and having a first end and a second end. The method further contemplates introducing the second end of the wire through the puncture in the patient's skin, placing at least a portion of the second end of the wire in contact the adipose tissue, generating an ultrasonic wave, transmitting the ultrasonic wave to the second end of the wire, creating cavitation bubbles in at least a portion of the targeted adipose tissue and liquefying at least a portion of the targeted adipose tissue. The method may further include monitoring the location of the wire either manually or by using diagnostic ultrasound equipment. The liquid included in the method may be a clysis solution, which may at least one of normal saline, lactated Ringer's solution and Krebs solution or may be Krebs-Ringer bicarbonate solution. The clysis may also include microbubbles. The clysis may further include an anesthetic preparation, lidocaine, for example. The anesthetic preparation may also include epinephrine. The clysis solution may also contain collagenase and/or lipase. The method, after removing the wire, may also include introducing a microsuction cannula through the puncture in the patient's skin, placing the microsuction cannula in proximity to the liquefied adipose tissue, applying suction to the microsuction cannula and aspirating the liquefied adipose tissue through the microsuction cannula. The method may further include marking the patient's skin to identify the area of treatment prior to infiltrating the adipose tissue with the liquid. The wire may be from 0.5 to 1.5 mm in diameter. The method may also involve letting the patient's body absorb the cavitated fat.

The present disclosure also contemplates a kit for carrying out a method of fat cavitation. The kit includes a surgical cutting instrument, a clysis solution, and an ultrasound device including a catheter, a wire disposed within the catheter, the wire being generally uniform in diameter and having a first end and a second end, a horn in communication with the wire and a generator in communication with the horn. The surgical cutting instrument may be a No. 11 blade knife. The surgical cutting instrument may also be a needle. The clysis solution may also include an anesthetic preparation, lidocaine, for example. The anesthetic preparation may also include epinephrine. The wire may be from 0.5 to 1.5 mm in diameter. The clysis solution may be at least one of normal saline, lactated Ringer's solution and Krebs solution or may be Krebs-Ringer bicarbonate solution. The clysis solution may also contain collagenase and/or lipase.

The reader will appreciate the foregoing details and advantages of the present disclosure, as well as others, upon consideration of the following detailed description of embodiments set forth in the disclosure. The reader also may comprehend additional details and advantages of the present disclosure upon using the method set forth in the present disclosure.

BRIEF DESCRIPTION OF THE FIGURES

FIG. 2 is an enlarged section view of the wire attachment portion of FIG. 1. (FIG. 2 from U.S. Pat. No. 4,920,954)

FIG. 3 is an enlarged perspective view of the ultrasonic device shown in FIG. 1. (FIG. 4 from U.S. Pat. No. 4,920,954)

FIG. 4 is an enlarged section view of a portion of FIG. 3. (FIG. 5 from U.S. Pat. No. 4,920,954)

FIG. 5 is disassembled perspective view generally of FIG. 4. (FIG. 6 from U.S. Pat. No. 4,920,954)

(FIGS. 7(a)-(c) from U.S. Pat. No. 4,920, 954)

DETAILED DESCRIPTION

Figures 1, 1A:
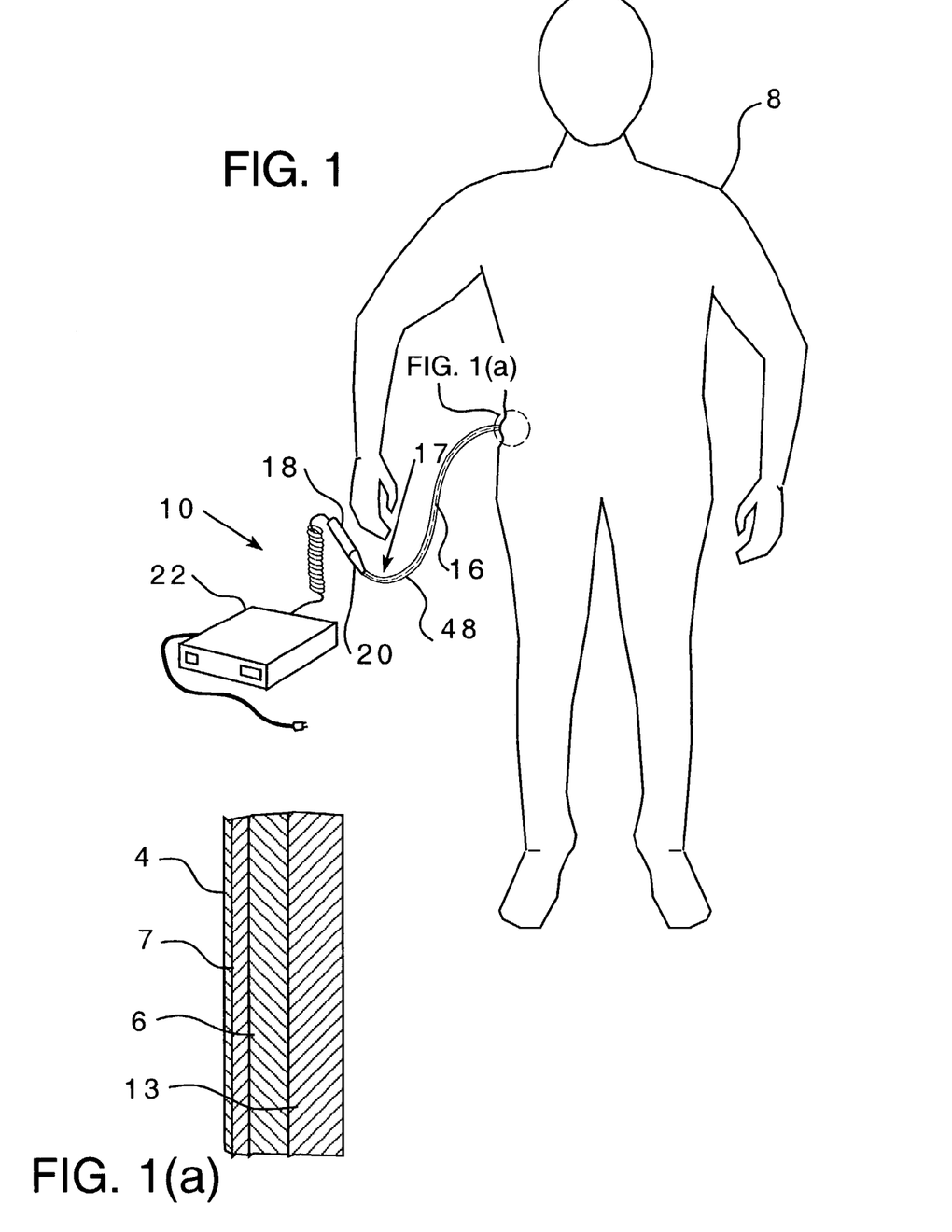
FIG. 1 depicts an apparatus used in performing a method of fat cavitation contemplated herein.
FIG. 1(a) depicts the layers of the skin, from the treated area in FIG. 1, in cross-section.

As previously mentioned, the device of U.S. Pat. No. 4,920,954, the device of U.S. Pat. No. 4,474,180, or any ultrasonic device including a wire, a catheter, a horn and a generator may be used to carry out the method contemplated herein. Such devices are common and well known to those of ordinary skill in the art. The device of the U.S. Pat. No. 4,920,954 is described for purposes of providing the reader with a detailed example of a device which may be used to carry out the procedure contemplated herein. The device of U.S. Pat. No. 4,920,954 is described in that patent as follows (with necessary edits and modifications to properly focus on the method contemplated herein): As illustrated in FIG. 1, a human being 8 is treated by an ultrasonic device 10 of the present disclosure. The epidermis covering the adipose tissue to be treated is typically marked prior to commencement of the procedure. In addition, the adipose tissue may be infiltrated with a clysis solution, which is described in more detail below. FIG. 1 (a) depicts the layers of skin in the area treated in FIG. 1.

An incision through the subcutaneous tissue within the area marked for treatment exposes the adipose tissue 13. The incision, which is approximately 2 mm in length, may be made with a No. 11 blade knife, needle or any other surgical cutting instrument appropriate for making this size incision, as would be known to one skilled in the art. For example, and in no way intended as a limitation, the opening may be achieved with a spinal needle.

The ultrasonic device 10 has a wire 16 which acts as a waveguide that is positionably disposed within a catheter assembly 17. The wire 16 is typically solid. The wire 16 is maneuvered to be proximate to targeted adipose tissue.

Figures 2, 3:
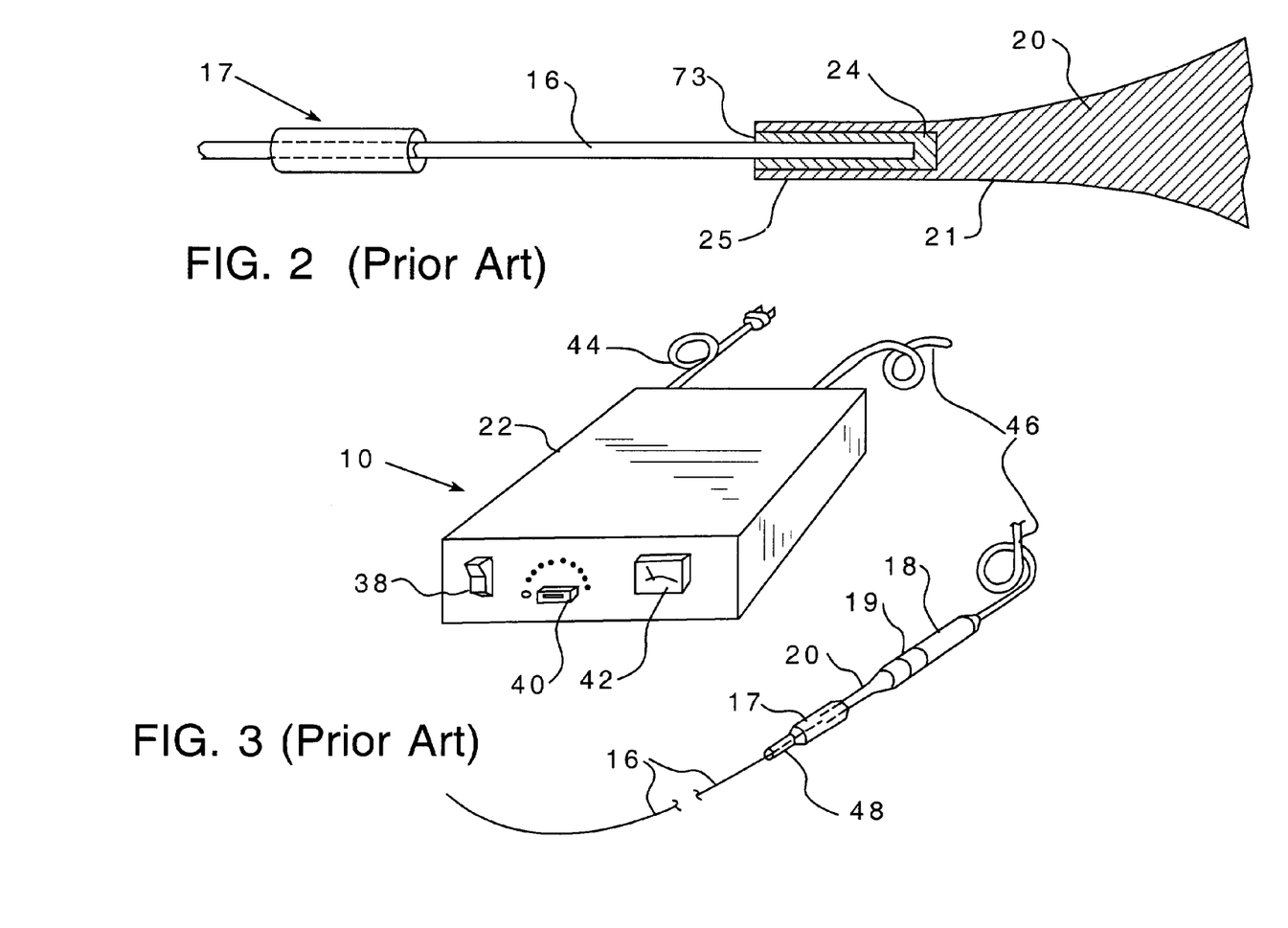

Referring now to FIGS. 1 through 4, device 10 also has a handpiece 18, that contains a piezoelectric or magnetostrictive converter or transducer 19 therein which produces ultrasonic energy and transmits it to the wire 16, and a generator 22 which energizes the transducer 19. Handpiece 18 has an exponential horn or tapered portion 20, which has a surface 21 that has an exponential concave profile. Handpiece 18 also has an elongate drilled hole 24 that receives an inner end of wire 16. A solder joint material 25 is present in the region between an inner surface of hole 24 and an outer surface of wire 16 adjacent thereto. The thickness of the solder material 25 shown in FIG. 2 is exaggerated for ease of illustration.

In a process of attaching the wire 16 to the horn 20, the mating surfaces of hole 24 and wire 16 are first coated with a brazable material such as nickel or copper by a plating process such as electroplating or electroless plating. With both mating surfaces now coated, the wire 16 can be brazed or soldered by conventional means, resulting in a strong continuous bond to the horn 20. Thus, the wire 16 and tapered portion 20 are joined, so as to prevent any relative distortion or deflection therebetween, and so as to form a continuous, non-interrupted metal material for ease of transmission of vibration. The joint at solder material 25 is long enough to withstand the vibration energy applied thereat and does not cause any substantial reflection of the waves of vibration passing therethrough.

A second alternative method of attachment of the wire 16 to the horn 20 is by a friction fit or shrink fit. In the process of manufacture, a hole 24 slightly smaller than the diameter of the wire 16 is first drilled into the end 73 of the horn 20. The end 73 of the horn 20 is heated and the wire 16 is cooled. With the wire 16 held securely, for example in a collet (not shown), the horn 20 is slowly forced or tapped onto the wire 16. When both wire 16 and horn 20 return to the ambient temperature, the wire 16 expands and the metal around the hole 24 contracts to form a bond strong enough to withstand the high energy of vibration.

Wire 16 is preferably composed of titanium metal or another suitable biocompatible rigid material. This wire may be flexible, such that it is capable of being bent to enter into areas into which it needs to fit. For use in the method contemplated herein, the solid wire 16 may be made from a titanium alloy and may have a diameter in the range of 0.5 to 1.5 millimeters (mm). It is to be understood that numerical ranges provided throughout the present disclosure are not intended in any way to limit the scope of the invention to those exact ranges. Rather, some deviation from those ranges is contemplated as falling within the scope of the present disclosure.

The sound losses in a bent wire are: Losses=K(D/R), where D is the diameter of the wire, R is the radius of the bend and K a constant. The larger the diameter of the wire or smaller the bend radius, the more the sound wave differs in the time it takes to move from one point to another through the length of the wire. The path length along the inside bend radius is shorter than that along the outside and this distorts the wave front. Furthermore, the stress on the metal also varies between the inner and outer circumference; the inner being under compression and the outer under tension. This difference in stress alters the density and therefore the speed of sound in the wire. All the above changes produce nonlinearity of transmission and result in heating, harmonics, and lateral motion. Accordingly, the diameter has to be kept as small as reasonably possible in order to minimize these losses.

Thinner wire, below 1 mm in diameter, although producing fewer losses due to a lower D/R ratio, becomes highly susceptible to transverse waves that naturally appear, even without bending or high amplitudes and the wire will vibrate laterally. This motion tends to stress the wire particularly at its point of attachment to the horn. While a wire having a diameter of 0.5 to 1.5 mm may be used, 1.0 to 1.5 mm is preferred and 1.2 to 1.5 mm is most preferred.

The frequency is important in that the stresses and heat dissipation increase in the wire as the sound frequency is raised. This is due to the greater acceleration of the wire molecules. Below about 20 kHz, however, high pitched noise may become objectionable. For a given power level, the lower the frequency, the higher the cavitation intensity. By way of example, and in no way intended as a limitation, the method of the present disclosure may employ a frequency of 23 to 50 kHz.

For a given length of wire 16 composed of a titanium material, for example, a maximum displacement of wire 16 at its outer tip portion would occur, thereby providing a maximum amount of cavitation or fluid bubble action for liquefying adipose tissue.

In FIG. 3, an enlarged view of generator 22 is shown. Generator 22 has an on-off switch 38, a power setting control knob 40 and a power meter 42. Generator 22 also has a power line 44 for insertion in a conventional 110 volt or 220 volt outlet, and a connecting line 46 which extends from generator 22 to handpiece 18.

In operation, an operator, such as a surgeon, monitors the power meter 42 and applies low power at knob 40, during the surgical maneuvering of the outer tip end portion of wire 16 toward the adipose tissue to be liquefied. Upon contact of the outer tip end portion of wire 16 with the adipose tissue, which is indicated by an increase in the reading of meter 42, the operator applies high power at knob 40 for generating cavitation adjacent to the adipose tissue for liquefying the adipose tissue.

Figure 4:
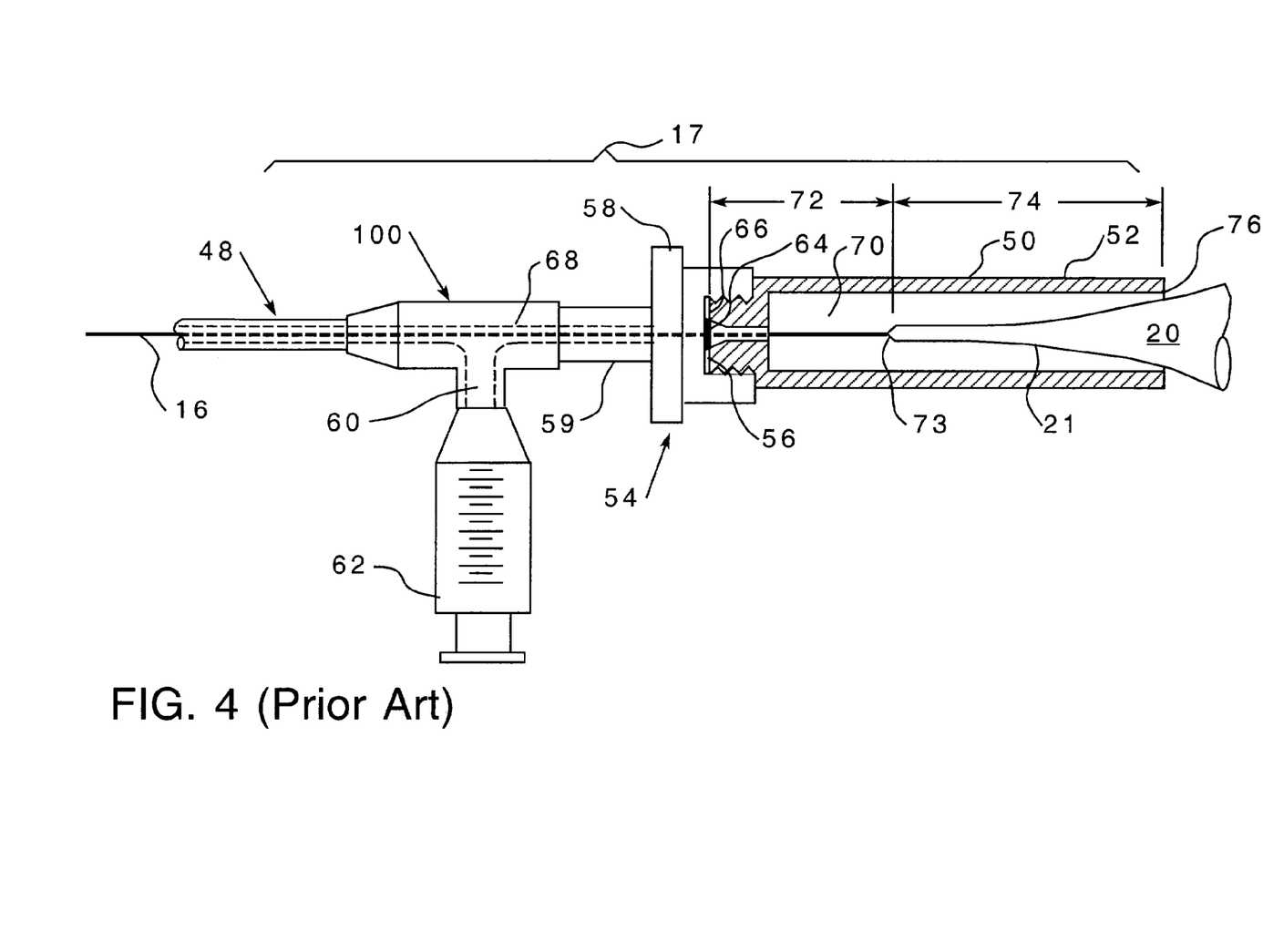

In FIG. 4, catheter assembly 17 includes a catheter tube 48, a container unit 50, a coupling unit 54, and a contrast fitting 100. The catheter tube 48 may be polytetrafluoroethylene or may have an inner surface of polytetrafluoroethylene or other inert material having a low coefficient of friction to slip easily over the wire 16. Container 50 includes a peripheral wall or sleeve 52 and a coupling unit 54. Coupling unit 54, which is somewhat similar to a coupling unit for a garden hose, has a fixed portion 56 which is fixedly connected to sleeve 52, and has a rotatable portion or knob portion 58 which is rotatable relative to fixed portion 56, in order to axially displace gliding sleeve 59 relative to fixed portion 56. Knob 58 is attached to portion 56 to permit rotation but no axial movement therebetween. Axial movement is imparted to sleeve 59 by rotation of knob 58. Catheter tube 48 is connected to contrast fitting 100 which is connected to portion 59 and moves relative to knob 58, for axial displacement of tube 48 relative to sleeve 52. In this way, by rotating knob 58, tube 48 is axially displaceable relative to wire 16, so that the outer tip portion of wire 16 can be slightly extended, when causing cavitation, beyond the outer tip portion of tube 48.

Rotatable portion 58 has a seal means (not shown) in order to prevent leakage from coupling 54. Fixed portion 56 is fixedly connected to the adjacent portion of sleeve 52 and has a seal means in the form of O-ring 66 to prevent leakage from coupling 54.

While the device of the U.S. Pat. No. 4,920,954 includes a contrast medium reservoir, a contrast medium is not employed in the method contemplated herein.

In FIG. 4, O-ring member 66 has an inner hole through which wire 16 passes. O-ring member 66 sealingly engages wire 16. The size of such hole in O-ring member 66 is exaggerated in FIG. 4 for ease of illustration. O-ring member 66 is located at a nodal point of wire 16 which is located at a selected dimension 72 away from the tip end face or attachment point 73 of tapered portion 20, as explained hereafter.

Container unit 50 also has a sealed connection 76 for connection of container unit 50 to tapered portion 20. Connection 76 may include an O-ring member on sleeve 52 which bears against a part of surface 21 of tapered portion 20. Connection 76 is at a nodal point of tapered portion 20 which is located at a selected dimension 74 away from the tip end face 73 of tapered portion 20, as explained hereafter.

O-ring member 66, which is at an axial nodal point of wire 16, is able to dampen the transverse force on wire 16 at that point when wire 16 is vibrated by the horn 20. O-ring member 66 does not substantially dampen the longitudinal vibration waves in wire 16. Thus, severe bending and relatively high stresses, at the region of wire 16 adjacent the attachment point to the end face 73 of the tapered portion 20, is avoided.

The nodal point in wire 16 at O-ring member 66 applies to both the transverse wave and longitudinal wave of vibration in wire 16. The nodal point has substantially no movement. An antinode point between two nodal points has a maximum movement. The point on wire 16 at the end face of tapered portion 20, or the wire attachment point, acts as an antinode point for the longitudinal wave of vibration, and acts as a nodal point for the unwanted transverse wave of vibration.

Figure 5:
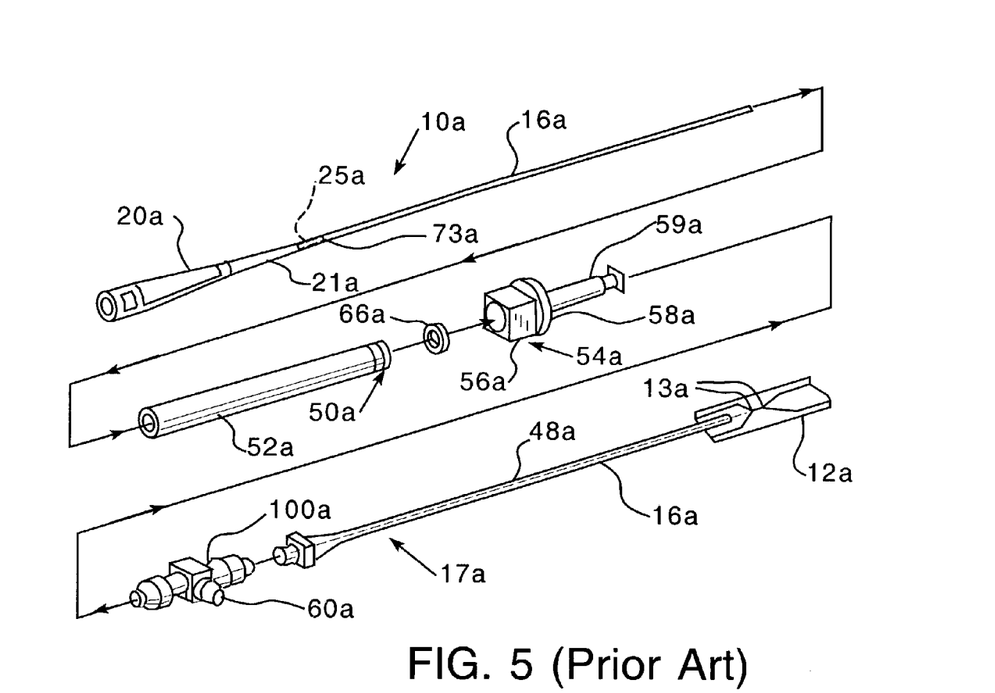

For purposes of further explanation, FIG. 5 provides a disassembled perspective view generally of that portion of ultrasonic device 10 shown in FIG. 4. Parts of device 10a, which correspond to similar parts of device 10, have the same numerals, but with a subscript "a" added thereto.

Device 10a includes a wire 16a, and a catheter assembly 17a. Device 10a has an exponential horn or tapered portion 20a, which has a surface 21a. Wire 16a is fixedly connected to tapered portion 20a by a solder joint 25a.

Wire 16a is composed of a titanium material. Wire 16a is a waveguide for longitudinal vibration waves from horn portion 20a. The longitudinal vibration waves cause an axial movement of the tip portion of wire 16a, thereby causing cavitation, which leads to liquefaction of the adipose tissue.

Catheter assembly 17a includes a catheter tube 48a, and a container or dampening unit 50a. Unit 50a has a sleeve or peripheral wall 52a and a coupling unit 54a. Unit 54a is used to axially displace wire 16a relative to catheter tube 48a, in order to extend an end portion of wire 16a, for cavitating adipose tissue. Coupling unit 54a has a fixed portion 56a, which is fixedly connected to sleeve 52a, and has a rotatable portion 58a, which is angularly movable relative to fixed portion 56a, for axially displacing catheter tube 48a.

Device 10a also has an O-ring 66a, which is positioned at a selected distance from the end face 73a of horn portion 20a. O-ring 66a is located at a nodal point of the longitudinal vibration wave which defines a nodal point of the transverse vibration wave, in order to minimize wire stresses at the end face 73a of horn portion 20a, and in order to prevent transverse movement or whipping of wire 16a at the location of the O-ring 66a.

Sleeve or dampening unit 50a has a connection to tapered horn portion 20a for assembly thereof.

Catheter tube 48a is composed of a suitable plastic material, such as polytetrafluoroethylene. Fitting 100a is composed of a stainless steel material. Sleeve 52a is composed of a suitable plastic material. Wire 16a is composed of a titanium material. Exponential horn 20a is composed of a titanium material. Coupling 54a is composed of a stainless steel or other suitable material.

Figure 6A:
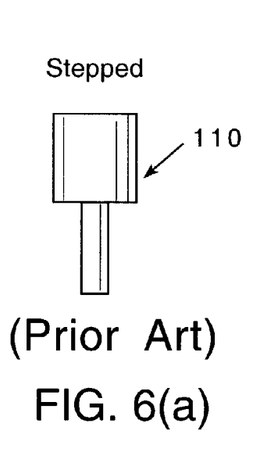
FIGS. 6(a) through 6(c) are perspective views showing various types of sonic horns which transmit and amplify the ultrasonic wave.
Figure 6B:
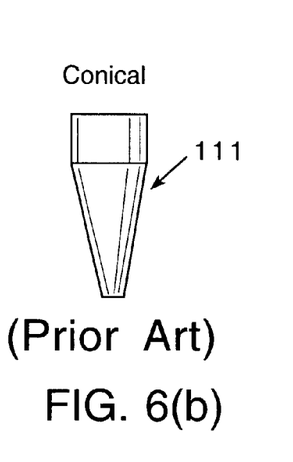
Figure 6C:
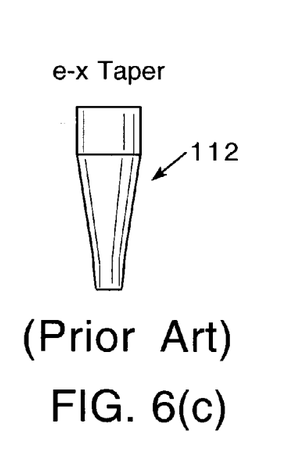

FIGS. 6(a) through 6(c) show various configurations of horns. In FIG. 6(a), a standard step horn 110 is shown which provides the greatest amplitude for laboratory sonic probes but is not the best choice for transmitting energy into wire of the diameter used in the present application. In FIG. 6(b), a conical shaped horn 111 is shown which is also less than ideal. In FIG. 6(c), the exponential horn 112 having a taper $e^{-x}$ was best for the present application since unwanted frequencies and harmonics were minimized and the titanium wire described previously could be operated above its previously maximum rated amplitude before breaking. U.S. Pat. No. 4,920,954, col. 6, line 58 to col. 11, line 56.

The following discussion is carried out with reference to the device of U.S. Pat. No. 4,920,954 as described above. However, as previously indicated any ultrasonic device including a wire, a catheter in which the wire is disposed, a horn and a generator may be employed. Such devices are common and well known to those of ordinary skill in the art.

In the performance of a method contemplated herein, an area of adipose tissue is targeted for liquefaction. To assist in locating the adipose tissue to be treated, an area of the patient's epidermis overlying the targeted adipose tissue 13 is marked or labeled.

The targeted adipose tissue prior to, or contemporaneous with, the initiation of fat cavitation, is infiltrated with a liquid, which may be a clysis solution. The clysis solution used may, for example, comprise either normal saline, lactated Ringer's solution or Krebs solution. Ringer's solution mixture typically contains normal saline and small amounts of potassium in addition to providing lactate. However, a number of variations of Ringer's solution are known and may be utilized in the present method. Similarly, numerous modifications of Krebs solution are known and may be used in the present method. One such composition of Krebs solution includes sodium chloride, potassium chloride, calcium chloride, magnesium chloride, sodium bicarbonate, collagenase, lipase, sodium phosphate and glucose. The clysis solution may also comprise a Krebs-Ringer bicarbonate solution.

The clysis solution, which mimics the body's normal physiological fluids, further augments the liquefaction of adipose tissue. Use of the Krebs-Ringer bicarbonate solution as the clysis solution enhances the lipolysis allowing the ultrasound to further disrupt the targeted adipose tissue 13. Accordingly, the clysis solution is injected under the subcutaneous layer 6 and, thus, infiltrates the targeted adipose tissue 13. In one embodiment of the present method, the clysis solution is injected about fifteen (15) minutes prior to initiation of the fat cavitation method. In addition to the foregoing, the clysis solution serves to dampen the buildup of localized heat. Accordingly, other liquids, for example, distilled water, may also be used in lieu of, or in addition to, a clysis solution.

A No. 11 (or similarly sized) blade knife or needle is used to penetrate the epidermis 4, dermis 7 and subcutaneous layer 6, creating a puncture and exposing the adipose tissue 13. A wire 16 is then introduced through the puncture in the skin. The wire 16 may be of any diameter sufficiently narrow enough to allow it to pass through the puncture, but is typically from 0.5 to 1.5 mm in diameter. The wire 16 may be of any length sufficient to allow it to reach the targeted adipose tissue 13, as discussed below. Typically, the length of the wire 16 will be 3 to 20 centimeters (cm). The targeted adipose tissue 13 should typically be approached from superficial (that adipose tissue closest to the dermis) to deep (that adipose tissue farthest from the dermis), resulting in cavitation and liquefaction of adipose tissue 13 from superficial to deep. In addition, the depth of wire penetration should typically be limited to from 2 mm to 3 or 4 cm from the outer surface of the skin.

After the second end of the wire 16b is inserted through the patient's skin, at least a portion of the wire 16 is positioned such that at least a portion of the second end of the wire 16b is proximate to the adipose tissue 13 targeted for cavitation. Ultrasonic waves are then generated, as described in U.S. Pat. No. 4,920,954. These ultrasonic waves are communicated through the wire to the second end of the wire 16b which then vibrates ultrasonically. The ultrasonically vibrating second end of the wire 16b results in cavitation of at least a portion of the adipose tissue 13. When adipose tissue cavitates, the molecules lose their arrangement, or are loosened in some manner, so that the solid becomes liquid.

As the targeted adipose tissue 13 cavitates and liquefies, the wire 16 is advanced or moved in various directions to contact and, thus, cavitate and liquefy additional adipose tissue. To avoid thermal damage, the wire 16 is moved constantly during the procedure. It should be noted that the ultrasonically vibrating second end of the wire 16b cavitates and liquefies not only adipose tissue which it contacts directly, but also cavitates and liquefies adipose tissue located up to approximately 3 mm away from the ultrasonically vibrating second end 16b.

As the wire 16 advances, cavitating and liquefying additional adipose tissue, a volume of liquefied adipose tissue accumulates. The human body is capable of processing and eliminating up to approximately 500 ml of this liquefied adipose tissue safely at one time. Thus, the present cavitation method may be carried out to liquefy 500 ml or less of liquefied adipose tissue. Because this liquefied adipose tissue will be naturally processed by the body, there is no need to physically remove it by a traditional liposuction method. Rather, the liquefied adipose tissue is left in place in the patient's body. The amount of adipose tissue liquefied may be approximated by monitoring the amount of clysis solution used. While some additional volume is contributed by the liquefied adipose tissue, the amount of clysis solution will provide guidance regarding the amount of adipose tissue liquefied. By way of example, and in no way intended to limit the present disclosure, about 200 ml of clysis solution will result in a total of about 230 to about 250 ml in total of clysis solution and liquefied adipose tissue. Thus, to reach the 500 ml maximum, approximately 400 ml of clysis solution should be used. Preferably, the present disclosure is performed in only one area of the body at a time in order to avoid exceeding the 500 ml limit. Because the procedure contemplated herein is minimally invasive and has a recovery period similar to that associated with other minimally invasive procedures such as microdermabrasion, the procedure may be repeated approximately every 2-3 weeks, with a goal to achieve circumference reduction and/or contouring of the treated part of the body.

During the time in which the surgeon moves the wire 16 about to contact the targeted areas of adipose tissue, it is imperative that he/she be able to closely follow and monitor the wire's 16 movement and location. One way in which this may be accomplished is simply by the surgeon using his/her fingers to manually feel the wire 16 and, thus, track its progression and location through the patient's skin. Because the wire 16 is disposed no more than 3 to 4 cm below the skin and readily susceptible to detection through feel, this manual method is easily carried out.

In addition to, or in place of, the manual method described above, the wire may be located and monitored throughout the duration of the procedure by employing diagnostic ultrasound equipment. The ultrasound equipment is simply trained on the area of the patient's body undergoing treatment. By closely monitoring the location of the wire, the surgeon may accurately target the location and amount of adipose tissue to be removed via the method described herein.

Microbubbles, which are small gas bubbles, may optionally be introduced to the clysis solution. The use of microbubbles is known, for example, in drug delivery systems. When introduced to the targeted adipose tissue 13, microbubbles aid in and accelerate the cavitation and liquefaction of that tissue.

Optionally, an anesthetic preparation may be administered to the patient, either separately or as an additive to the clysis solution. This anesthetic preparation may be any known local anesthetic appropriate for surgical procedures, for example, lidocaine 2%. The local anesthetic decreases or eliminates any discomfort that the patient might otherwise feel during the procedure contemplated herein. To enhance the effect and duration of the anesthetic, epinephrine may also optionally be added to the anesthetic preparation. For example, the epinephrine may be in a concentration of 1:100,000 (0.01 mg/ml). The epinephrine, through vasoconstriction, helps to keep the lidocaine localized, thus facilitating its anesthetic effects for an increased period of time. The epinephrine may also stimulate the release of fatty acids and glycerol from adipose tissue. As with the anesthetic alone, the anesthetic/epinephrine combination may be administered to the patient either in alone or as an additive to the clysis solution. By way of example only, and in no way intended to limit the present disclosure, the clysis solution may be comprised of 500 ml of Krebs-Ringer solution containing 12.5 mEq $NaHCO_3$, 1 mg epinephrine and 200 mg of lidocaine. The clysis solution may also contain collagenase which may weaken the fibrous tissue holding the adipose tissue. Lipase aids in hydrolyzing the adipose tissue.

After the desired amount of adipose tissue has been cavitated and liquefied, the wire 16 is removed from the same puncture through which it was introduced. Optionally, a microsuction cannula (not shown) may then be introduced into the patient through the puncture. The microsuction cannula may be of any gauge providing it with a sufficiently small enough outer diameter to allow it to pass through the puncture. Typically, a microsuction cannula having a diameter of 2 mm may used. After insertion, the microsuction cannula is placed in proximity to the liquefied adipose tissue. Upon application of suction, at least a portion of the liquefied adipose tissue may then be removed from the patient's body via aspiration through the microsuction cannula. The cannula may be attached to a Toomey syringe or to a suction apparatus.

Following liquefaction of the desired amount of adipose tissue, the wire is removed from the same puncture through which it was introduced. The puncture is then closed with a small adhesive strip with a gauze pad of the type typically used to cover minor cuts and abrasions.

Because only a small puncture is required with the present method, a patient undergoing the fat cavitation method described herein suffers no scarring. In fact, a patient's experience with the procedure described herein is similar to that of receiving an injection. Conventional liposuction methods usually cause a 4 mm scar resulting from the incision needed to insert the liposuction tubing into the patient. Even larger scars, e.g., 6 mm, are seen when ultrasound is added to the conventional methods. This increase in scar size results from the requisite insertion of an ultrasonic transducer.

The method described herein is contemplated as being carried out on an outpatient basis and may be performed in the physician's office. Thus, the patient can receive the minimally invasive fat cavitation treatment and then go about his/her normal daily activities. This is due, in large part, to the fact that the patient receives only a small puncture mark, 1-2 mm in size, for example, rather than the one-half inch (12.70 mm) scar seen with other liposuction methods which incorporate ultrasound. Further, the 4-6 week healing period seen with the more invasive liposuction methods (with and without ultrasound), which remove larges volumes of adipose tissue, is not seen with the present method which calls for the removal of no more than about 500 ml of adipose tissue during any one treatment session. If more than 500 ml of adipose tissue is to be removed, the present method may be repeated through additional patient visits to the surgeon's office until the desired amount of adipose tissue is ablated.

An additional method contemplated by the present disclosure includes introducing the wire 16 and catheter tube 48 through the skin and then providing irrigation by introducing clysis solution, which may include microbubbles, to the targeted adipose tissue 13 through the catheter tube 48 prior to activation of the ultrasound. The advantage of this method is the need for only one puncture of the patient's skin to introduce both the clysis solution and the wire 16. Thus, the need for two separate punctures—the first to introduce the clysis solution and the second to introduce the wire 16—is avoided.

It is to be understood that the present description illustrates those aspects relevant to a clear understanding of the disclosure. Certain aspects that would be apparent to those skilled in the art and that, therefore, would not facilitate a better understanding have not been presented in order to simplify the present disclosure. Although the present disclosure has been described in connection with certain embodiments, those skilled in the art will, upon considering the foregoing disclosure, recognize that many modifications and variations may be employed. It is intended that all such variations and modifications are covered by the foregoing description and following claims.

We claim:

1. A method of fat cavitation, comprising:
infiltrating subcutaneous adipose tissue with a liquid comprising microbubbles up to about 400 ml and at least one of normal saline, lactated Ringer's solution and Krebs solution;
creating a puncture in the patient's skin;
providing a wire, the wire being generally uniform in diameter and having a first end and a second end;
introducing the second end of the wire through the puncture in the patient's skin;
placing at least a portion of the second end of the wire in contact with the subcutaneous adipose tissue;
generating an ultrasonic wave;
transmitting the ultrasonic wave to the second end of the wire;
creating cavitation bubbles in at least a portion of the targeted adipose tissue; and
liquefying at least a portion of the targeted adipose tissue up to a combined liquefied adipose tissue and infiltrated liquid of about 500 ml.

2. The method of claim 1 further comprising monitoring the location of the wire.

3. The method of claim 2 wherein the monitoring comprises feeling the wire manually.

4. The method of claim 2 wherein the monitoring comprises using diagnostic ultrasound equipment.

5. The method of claim 1 wherein the liquid comprises a clysis solution comprising Kregs-Ringer bicarbonate solution.

6. The method of claim 5 wherein the clysis solution further comprises collagenase.

7. The method of claim 5 wherein the clysis solution further comprises lipase.

8. The method of claim 1 wherein the infiltrated liquid further comprises an anesthetic preparation.

9. The method of claim 8 wherein the anesthetic preparation comprises lidocaine.

10. The method of claim 9 wherein the anesthetic preparation further comprises epinepbrine.

11. The method of claim 1 comprising:
removing the wire from the patient;
introducing a microsuction cannula through the puncture in the patient's skin;
placing the microsuction cannula in proximity to the liquefied adipose tissue;
applying suction to the microsuction cannula; and
aspirating the liquefied adipose tissue through the microsuction cannula.

12. The method of claim 1 further comprising marking the skin of the patient to identify the area of treatment prior to infiltrating the adipose tissue with the liquid.

13. The method of claim 1 wherein the wire is 0.5 to 1.5 mm in diameter.

14. The method of claim 13 wherein the wire is 1.0 to 1.5 mm in diameter.

15. The method of claim 13 wherein the wire 1.2 to 1.5 mm in diameter.

16. A kit for carrying out a method of subcutaneous fat cavitation, comprising:
a surgical cutting instrument sized for making an incision of about 2 mm or less;
a clysis solution comprised of microbubbles and at least one of normal saline, lactated Ringer's solution, Krebs solution and Krebs-Ringer bicarbonate solution; and
an ultrasound device, comprising
a catheter;
a wire disposed within said catheter, said wire having a generally uniform diameter of about 0.5 to 1.5 mm and having a first end and a second end;
a horn in communication with said wire; and
a generator in communication with said horn.

17. The kit of claim 16 wherein said surgical cutting instrument comprises a No. 11 blade knife.

18. The kit of claim 16 wherein said surgical cutting instrument comprises a needle.

19. The kit of claim 17 wherein the clysis solution further comprises an anesthetic preparation.

20. The kit of claim 19 wherein the clysis solution further comprises lidocaine.

21. The kit of claim 20 wherein said anesthetic preparation further comprises epinephrine.

22. The kit of claim 16 wherein said clysis solution comprises collagenase.

23. The kit of claim 16 wherein said clysis solution comprises lipase.

* * * * *

UNITED STATES PATENT AND TRADEMARK OFFICE
CERTIFICATE OF CORRECTION

PATENT NO. : 7,374,551 B2  Page 1 of 1
APPLICATION NO. : 10/370214
DATED : May 20, 2008
INVENTOR(S) : Marc D. Liang and Krishna R. Narayanan It is certified that error appears in the above-identified patent and that said Letters Patent is hereby corrected as shown below:

Column 2, Line 47
"ire.," should read "i.r.,"

Claim 10
Column 12, Line 6
"epinepbrine" should read "epinephrine"

Signed and Sealed this
Eleventh Day of September, 2012

David J. Kappos
*Director of the United States Patent and Trademark Office*